United States Patent
Bolze et al.

(10) Patent No.: US 11,427,672 B2
(45) Date of Patent: *Aug. 30, 2022

(54) STORAGE-STABLE POLYURETHANE CASTING COMPOUND FOR EMBEDDING HOLLOW FIBRES IN THE PRODUCTION OF FILTER ELEMENTS

(71) Applicant: BASF SE, Ludwigshafen am Rhein (DE)

(72) Inventors: Patrick Bolze, Lemfoerde (DE); Andre Kamm, Lemfoerde (DE); Thomas Mathieu, Lemfoerde (DE); Ralf Fritz, Lemfoerde (DE); Gunther Lukat, Lemfoerde (DE)

(73) Assignee: BASF SE, Ludwigshafen am Rhein (DE)

( * ) Notice: Subject to any disclaimer, the term of this patent is extended or adjusted under 35 U.S.C. 154(b) by 203 days.

This patent is subject to a terminal disclaimer.

(21) Appl. No.: 16/610,436

(22) PCT Filed: Apr. 27, 2018

(86) PCT No.: PCT/EP2018/060832
§ 371 (c)(1),
(2) Date: Nov. 1, 2019

(87) PCT Pub. No.: WO2018/202566
PCT Pub. Date: Nov. 8, 2018

(65) Prior Publication Data
US 2021/0163659 A1    Jun. 3, 2021

(30) Foreign Application Priority Data

May 5, 2017 (EP) .................... 17169699

(51) Int. Cl.
| | |
|---|---|
| C08G 18/66 | (2006.01) |
| C08G 18/48 | (2006.01) |
| C08G 18/42 | (2006.01) |
| C08G 18/22 | (2006.01) |
| C08G 18/12 | (2006.01) |
| C08G 18/32 | (2006.01) |
| C08G 18/36 | (2006.01) |
| C08G 18/16 | (2006.01) |
| C08G 18/18 | (2006.01) |
| A61M 1/00 | (2006.01) |
| C02F 1/00 | (2006.01) |
| C02F 1/44 | (2006.01) |

(52) U.S. Cl.
CPC .......... *C08G 18/227* (2013.01); *C08G 18/12* (2013.01); *C08G 18/161* (2013.01); *C08G 18/1825* (2013.01); *C08G 18/22* (2013.01); *C08G 18/3206* (2013.01); *C08G 18/3281* (2013.01); *C08G 18/36* (2013.01); *C08G 18/4288* (2013.01); *C08G 18/48* (2013.01); *C08G 18/4829* (2013.01); *C08G 18/6674* (2013.01); *C08G 18/6696* (2013.01); *A61M 1/00* (2013.01); *C02F 1/00* (2013.01); *C02F 1/441* (2013.01); *C08G 2340/00* (2013.01)

(58) Field of Classification Search
CPC ...... C08G 18/227; C08G 18/36; C08G 18/32; C08G 18/48; C08G 18/12; C08G 18/22; C08G 18/1825; C08G 18/161; B01D 63/02; C02F 1/00; C02F 1/441; A61M 1/00

See application file for complete search history.

(56) References Cited

U.S. PATENT DOCUMENTS

| | | |
|---|---|---|
| 3,962,094 A | 6/1976 | Davis |
| 4,224,164 A | 9/1980 | Brauer et al. |
| 5,045,623 A | 9/1991 | Horn et al. |

(Continued)

FOREIGN PATENT DOCUMENTS

| | | |
|---|---|---|
| DE | 155777 A3 | 7/1982 |
| DE | 69026849 T2 | 12/1996 |
| DE | 102011078170 A1 | 12/2011 |
| EP | 329473 A2 | 8/1989 |

(Continued)

OTHER PUBLICATIONS

English translation of International Search Report for International Application No. PCT/EP2018/060832, dated Sep. 10, 2018, 2 pages.

(Continued)

*Primary Examiner* — Michael L Leonard
(74) *Attorney, Agent, or Firm* — ArmstrongTeasdale LLP

(57) ABSTRACT

Disclosed are polyurethane encapsulating compounds for embedding hollow fibers of filter elements, obtainable by mixing a polyol component (A) and an isocyanate component (B), including at least one aromatic isocyanate, to give a reaction mixture and reacting the mixture to completion to give the polyurethane encapsulating compound. The polyol component (A) includes at least one fatty-acid-based polyol (a1) having a hydroxyl number of greater than 50 to less than 500 mg KOH/g and a functionality of from 2-6, and at least one bismuth catalyst (a2), obtainable by mixing a bismuth carboxylate (a2-1) with an amine compound (a2-11) having at least one tertiary nitrogen atom and at least one isocyanate-reactive hydrogen atom. The molar ratio of bismuth to amine compound (a2-11) is 1:0.5-1:50. Also disclosed are methods for producing filter elements using the polyurethane encapsulating compounds and to uses of the polyurethane encapsulating compounds for the embedding of hollow fibers.

13 Claims, No Drawings

(56) References Cited

U.S. PATENT DOCUMENTS

| | | |
|---|---|---|
| 5,071,887 A | 12/1991 | Nakagawa et al. |
| 5,306,798 A | 4/1994 | Horn et al. |
| 5,451,629 A | 9/1995 | Jacobs |
| 6,776,909 B2 | 8/2004 | Hahmann et al. |
| 8,802,808 B2 * | 8/2014 | Reese ............... C08G 18/6696 528/76 |
| 2016/0200888 A1 * | 7/2016 | Duvall ............... C08G 18/4027 521/129 |

FOREIGN PATENT DOCUMENTS

| | | |
|---|---|---|
| EP | 413265 A2 | 2/1991 |
| EP | 538673 A2 | 4/1993 |
| EP | 844015 A2 | 5/1998 |
| EP | 2081973 A1 | 7/2009 |
| WO | 2016114876 A1 | 7/2016 |
| WO | 2018202564 A1 | 11/2018 |

OTHER PUBLICATIONS

European Search Report for EP Patent Application No. 17169699.0, dated Aug. 29, 2017, 3 pages.

* cited by examiner

STORAGE-STABLE POLYURETHANE CASTING COMPOUND FOR EMBEDDING HOLLOW FIBRES IN THE PRODUCTION OF FILTER ELEMENTS

CROSS-REFERENCE TO RELATED APPLICATIONS

This application is a U.S. National Phase Application of PCT/EP2018/060832, filed Apr. 27, 2018, which claims the benefit of priority to EP Application No. 17169699.0, filed May 5, 2017, the contents of which are hereby expressly incorporated by reference in their entirety.

The present invention relates to polyurethane encapsulating compounds for the embedding of hollow fibers of filter elements, obtainable by mixing a polyol component (A) and an isocyanate component (B), comprising at least one aromatic isocyanate, to give a reaction mixture and reacting the mixture to completion to give the polyurethane encapsulating compound, wherein the polyol component (A) comprises at least one fatty-acid-based polyol (a1) having a hydroxyl number of greater than 50 to less than 500 mg KOH/g and a functionality of from 2 to 6, and at least one bismuth catalyst (a2), obtainable by mixing a bismuth carbon/late (a2-I) with an amine compound (a2-II) having at least one tertiary nitrogen atom and at least one isocyanate-reactive hydrogen atom, wherein the molar ratio of bismuth to the amine compound (a2-II) is 1:0.5 to 1:50. The present invention further relates to a method for producing filter elements using the polyurethane encapsulating compounds and to the use of the polyurethane encapsulating compounds for the embedding of hollow fibers.

The use of polyurethane encapsulating compounds for the embedding of hollow fibers of filter elements is known, especially for filters that are used in the medical sector, such as the use as embedding material for hollow fibers in dialyzers, and this has been described, for example, in EP844015 B1. The advantage of the polyurethane encapsulating compounds composed of polyurethane is that it is possible to incorporate a proportion by volume of hollow fibers into the dialyzer and achieve an optimal impregnation of the hollow fibers. In addition, the polyurethane described for the production of the filters is hydrolysis-stable, survives the process of superheated steam sterilization undamaged, and in particular has no toxic potential. However, in order to achieve good and rapid curing and a high productivity, the use of catalysts is necessary.

The raw materials for preparing the polyurethane encapsulating compounds are typically premixed, usually as isocyanate component and polyol component. The manufacturer of the filter elements in that case merely has to mix the two components in a suitable ratio in order to obtain the polyurethane encapsulating compounds. The isocyanate component and the polyol component are generally transported to the processor in drums or tankers. Several days or months often pass between the preparation of the components and the processing thereof. However, the reactivity of the polyol component with the isocyanate component should not change during this period of time, so that a consistent increase in viscosity is guaranteed, and hence consistent impregnation of the hollow fibers and also curing and productivity.

U.S. Pat. No. 3,962,094 describes the use of catalyst-free polyurethane systems for preparing the polyurethane encapsulating compounds. Although these do have unchanging reactivity, the low reactivity means long cycle times and low productivity have to be accepted.

The use of aminic catalysts such as 1,4-diazabicyclo[2.2.2]octane for preparing polyurethane encapsulating compounds is likewise known. Yet since these catalysts exhibit high migration properties and can escape from the polyurethane obtained, they are not usable for medical application. In order to avoid this drawback, U.S. Pat. No. 4,224,164 discloses the use of N,N,N",N"-tetrakis(2-hydron/propyl)ethylenediamine. This catalyst has isocyanate-reactive groups and is therefore integrated into the polyurethane network, and so it cannot migrate. The catalytic properties of this incorporable catalyst can considerably raise the reactivities, but cycle times of industrial interest can be obtained only with concentrations of greater than 40% by weight in the polyol component. This high proportion of N,N,N",N"-tetrakis(2-hydron/propyl)ethylenediamine raises the viscosity of the reaction mixture for preparing the polyurethane encapsulating compound so greatly that optimal impregnation of the hollow fibers is no longer guaranteed.

DD-A-155777 discloses the use of tin compounds as catalysts for the preparation of polyurethane encapsulating compounds for dialyzers. The catalysts described in DD-A-155777 give a high and constant reactivity, and have established themselves, alongside other organotin compounds, as a standard for PU polyurethane encapsulating compounds in industry. Mention may be made, by way of example, of EP 2 081 973, EP 538 673, EP 413 265 and EP 329473. Because of the toxic potential of organotin compounds and the corresponding REACH classifications, the industry is searching for novel catalysts. However, all common metal catalysts display insufficient storage stability in polyol components which comprise fatty acid polyols required for the necessary hydrophobicity, such as castor oil. This leads to varying reaction times during the curing of the polyurethane encapsulating compounds depending on the storage duration. This is not accepted by the manufacturers of the filter elements.

The object of the present invention was therefore that of providing storage-stable components for preparing polyurethane encapsulating compounds for embedding hollow fibers of filter elements, wherein no toxic materials are used, no toxic materials are emitted from the polyurethane encapsulating compound even under sterilization conditions, and a uniformly rapid reaction time can be maintained. The curing performance should ideally correspond to that of the standard tin catalysts here.

The present object was achieved by polyurethane encapsulating compounds for embedding hollow fibers of filter elements, obtainable by mixing a polyol component (A) and an isocyanate component (B), comprising at least one aromatic isocyanate, to give a reaction mixture and reacting the mixture to completion to give the polyurethane encapsulating compound, wherein the polyol component (A) comprises at least one fatty-acid-based polyol (a1) having a hydroxyl number of greater than 50 to less than 500 mg KOH/g and a functionality of from 2 to 6, and at least one bismuth catalyst (a2), obtainable by mixing a bismuth carbon/late (a2-I) with an amine compound having at least one tertiary nitrogen atom and at least one isocyanate-reactive hydrogen atom, wherein the molar ratio of bismuth to the amine compound (a2-II) is 1:0.5 to 1:50.

The polyurethane encapsulating compounds according to the invention are preferably compact and are preferably used for the embedding of hollow fibers for filter elements, that is to say it is suitable as an embedding compound for hollow fibers for filter elements. Compact polyurethane encapsulating compounds are understood to be polyurethane encapsulating compounds having a density generally of from 0.8 g/l to 1.3 g/l, preferably from 0.9 g/l to 1.1 g/l. The polyurethane encapsulating compounds according to the invention, after curing has been performed, generally display a Shore D hardness of from 40 to 80. However, the encapsulating compounds according to the invention preferably have a Shore D hardness of from 55 to 75. Particular preference is given, for example for applications as encapsulating compound in dialysis filters, to a Shore D hardness of from 58 to 70. Shore D hardness relates to DIN 53505 at a temperature of 23° C. Those skilled in the art will choose the composition of the encapsulating compounds accordingly, for example the nature and amount of the high-functionality polyols, for example of the polyols (a3).

During the production of the filter elements, the polyol component (A) and the isocyanate component (B) is preferably mixed and placed into a mold comprising hollow fibers. The encapsulating compound here is particularly preferably introduced into a hollow body which is rotating in a centrifuge and comprises hollow fibers. As a result of centrifugal force, the liquid reaction mixture is transported to each of the two ends of the filter element while surrounding the hollow fibers, and cures to form a compact, essentially clear encapsulation.

The curing step takes place without further assistance by reaction of the NCO groups with reactive hydrogen atoms, especially of the OH groups, optionally at elevated temperature. The curing step is complete as soon as the encapsulating compound has largely reached its final properties, especially its hardness and its stability.

By means of a subsequent cutting process, the openings of the hollow fibers are usually exposed. The filter element is generally ready for use after a cleaning and sterilization process.

By means of the method according to the invention, it is possible to prepare encapsulating compounds that can be sterilized by superheated steam and are non-cytotoxic, and can be used for example as a water filter in the treatment or purification of drinking water or for example as a dialysis filter in the medical-technical sector. At the same time, using the polyurethane encapsulating compounds according to the invention, complex structures can be formed and by way of example a high fiber count of more than 12 000 fibers per filter, as required in dialysis filters, can be completely surrounded. In addition, the polyurethane encapsulating compounds according to the invention are hot sterilizable or wet sterilizable, for example by using peracetic acid, and display no migration of cytotoxic compounds, for instance amine compounds.

The cured polyurethane encapsulating compounds are resistant to disinfectants. In particular, the encapsulating compounds according to the invention exhibit a low absorption of water vapour or boiling hot water. The polyurethane encapsulating compounds according to the invention can be cut over a period of two weeks without formation of fine dust which otherwise may block the pores of the hollow fibers used for the actual filtration. The cured polyurethane encapsulating compounds according to the invention are preferably transparent, non-cytotoxic, and preferably have good adhesion to other materials that typically serve as filter housing, for instance polycarbonates, at elevated temperatures and over a relatively long period of time. The polyurethane encapsulating compounds are stable with respect to percarboxylic acids, and so shaped bodies made of such polyurethane encapsulating compounds can be sterilized, for example, with peracetic acid. The polyurethane encapsulating compounds according to the invention display high hydrophobicity and a sufficient crosslinking density.

The still free-flowing polyurethane encapsulating compounds can be also be cast without foam formation. At the same time, the polyurethane encapsulating compounds according to the invention, immediately after mixing of the reactive components, display a low mixed viscosity. The polyurethane encapsulating compounds are already cuttable after 2 hours, yet they do not undergo significant further curing, and so they can still be cut even after more than 24 hours. It is also advantageous that the encapsulating compounds according to the invention and based on polyurethane are processable with all customary types of hollow fiber, such as cuprophane, polysulfone, polycarbonate or cellulose fibers, and the polycarbonates used most often as materials of the filter housing do not require any pretreatment by corona discharge prior to the processing for improving the adhesion strength.

The present invention also further relates to a method for producing the polyurethane encapsulating compounds according to the invention. To this end, polyol component (A) and isocyanate component (B) are mixed to give a reaction mixture and left to react to completion to form the polyurethane encapsulating compound. Mixing may be carried out mechanically using a stirrer or a stirring screw or under high pressure in what is known as the countercurrent injection process. Here, in the context of the invention, the mixture of components (A) and (B) is called the reaction mixture for reaction conversions of less than 90%, based on the isocyanate groups.

The polyol component (A) here comprises (a1) at least one fatty-acid-based polyol, preferably having a hydroxyl number of greater than 50 to less than 500 mg KOH/g and a functionality of at least 2, at least one bismuth catalyst (a2), obtainable by mixing a bismuth carbon/late (a2-I) with an amine compound (a2-II) having at least one tertiary nitrogen atom and at least one isocyanate-reactive hydrogen atom, wherein the molar ratio of bismuth to the amine compound (a2-II) is 1:0.5 to 1:50.

OH functionality is to be understood here in the context of the present invention to be the number of alcoholic, acylatable OH groups per molecule. If the particular component is composed of a compound having defined molecular structure, the functionality is given by the number of OH groups per molecule. If a compound is prepared by ethoxylation or propoxylation of a starter molecule, the OH functionality is given by the number of reactive functional groups, for example OH groups, per starter molecule.

Suitable fatty-acid-based polyols are preferably those having a hydroxyl number of greater than 50 to less than 500 mg KOH/g, particularly preferably 100 to 300 mg KOH/g and especially 100 to 200 mg KOH/g, and a functionality of at least 2. The OH functionality of the fatty-acid-based polyols is preferably in the range from 2 to 3. The OH functionality of the fatty-acid-based polyols is particularly preferably from 2.3 to 3 and very particularly preferably from 2.6 to 3.

A fat-based polyol may be a fat, an oil, a fatty acid or a fatty acid derivative, or be obtained from the aforementioned compounds by physical or chemical modification. Fat-based polyols according to the definition mentioned above are known per se to those skilled in the art or can be obtained by methods known per se.

Examples of a fat-based polyol include vegetable oils and derivatives thereof. Vegetable oils can vary in their composition and exist in various grades of purity. Preference is given in the context of this invention to vegetable oils that satisfy the provisions of the German Pharmacopeia (Deutsches Arzneibuch, DAB). Component a1) very particularly preferably comprises at least one fat-based polyol which is a vegetable oil and complies with DAB-10.

Fat-based polyols that can be used are also commonly known fatty acids, preferably natural fatty acids, particularly preferably vegetable fatty acids, especially unsaturated vegetable fatty acids, and also derivatives thereof such as the esters with mono-, di-, and/or trialcohols, as long as the further properties with respect to molecular weight and OH functionality are fulfilled.

However, examples of fat-based polyols that can be used also include ring-opened epoxidized or oxidized fatty acid compounds and/or adducts of fatty acid compounds and alkylene oxides. Preference is given to hydroxylated fatty acids and/or hydroxylated fatty acid derivatives that are obtainable by the aforementioned methods.

The adducts of OH functional fat-based compounds, for example castor oil or hydroxylated vegetable oils, and alkylene oxides can be prepared by commonly known alkoxylation of the compounds with, for example, ethylene oxide, propylene oxide and/or butylene oxide at temperatures of from 80 to 130° C. and pressures of from 0.1 to 1 MPa, optionally in the presence of customary catalysts such as alkali metal hydroxides or alkali metal alkoxides.

Furthermore, fat-based polyols that can be used are also hydroxylated fatty acid compounds based on rapeseed oil, soya oil, colza oil, olive oil and/or sunflower oil and/or those based on oleic and/or linoleic acid. Suitable fat-based polyols are in particular polyols based on hydroxylated soya oil.

Preference is additionally given to triglycerides of fatty acids that have an OH functionality of from 2 to 3. Particular preference is given to the triglyceride of ricinoleic acid, optionally in a mixture with triglycerides which comprise further fatty acids, for example linoleic acid and/or palmitic acid.

The fat-based polyol used is particularly preferably a vegetable oil without chemical modification. Particular preference is given to castor oil or the alkoxylation product of castor oil, in particular castor oil. The fat-based polyol is especially preferably castor oil which satisfies the provisions of the German Pharmacopeia according to DAB 10. In one particularly preferred embodiment, the component (a1) used is exclusively castor oil.

Component (a1) preferably has a low water content, for example less than 0.2% by weight. A water content of component (a1) of less than 0.1% by weight is preferred. If a natural oil, by way of example castor oil, is used as component (a1), its use is typically preceded by a purification, which may especially include removal of suspended substances and dewatering. Natural oils freed of suspended substances and having the abovementioned water content are particularly suitable as component (a1).

The bismuth catalyst (a2) is obtainable by mixing a bismuth carboxylate (a2-I) with an amine compound (a2-II) having at least one tertiary nitrogen atom and at least one counterpart isocyanate-reactive hydrogen atom. The molar ratio of bismuth to the amine compound (a2-II) here is 1:0.5 to 1:50, preferably 1:1 to 1:20, particularly preferably 1:1 to 1:10 and especially 1:2 to 1:5.

In the bismuth carboxylates (a2-I), bismuth is preferably in the oxidation state of 2 or 3, especially 3. For salt formation, carboxylic acids used are preferably carboxylic acids having 6 to 18 carbon atoms, particularly preferably 8 to 12 carbon atoms. Examples of particularly suitable bismuth salts are bismuth(III) neodecanoate, bismuth 2-ethylhexanoate and bismuth octanoate; bismuth(III) neodecanoate is particularly preferably used.

To prepare the bismuth catalyst according to the invention, the bismuth carboxylate (a2-I) is admixed with the amine compound (a2-II), preferably at a temperature of 10 to 120° C., particularly preferably 20 to 100° C. and especially 50 to 80° C. The temperature is preferably selected here such that the amine compound (a2-II) is liquid. The mixing is preferably effected with stirring. In one preferred embodiment, the mixture is stirred at the mixing temperature at least for a further 5 minutes, particularly preferably 10 to 120 minutes and especially 10 to 60 minutes, and subsequently allowed to cool. If required, an additional solvent may be added, for example glycols such as diethylene glycol or monoethylene glycol. Preferably, besides the compounds (a2-I) and (a2-II), less than 100% by weight, preferably less than 50% by weight, based on the total weight of compounds (a2-I) and (a2-II), further compounds are added to the mixture of bismuth carboxylate (a2-I) and amine compound (a2-II) during the preparation of the bismuth catalyst (a2); the bismuth catalyst (a2) is in particular prepared prior to the preparation of polyol component (A) and hence prior to the addition of the fatty-acid-based polyol (a1).

The amine compound (a2-II) used may be at least one amine compound having at least one tertiary nitrogen atom and at least one isocyanate-reactive hydrogen atom. The amine compounds having at least one tertiary nitrogen atom preferably have a hydroxyl number of from 500 to 1200 mg KOH/g and an isocyanate functionality of at least 3, preferably 3 to 8 and particularly preferably 3 to 6. That means that compound (a2) has at least 3, preferably 3 to 8 and particularly preferably 3 to 6 hydrogen atoms that are reactive toward isocyanate groups. Compounds (a2-II) are preferably obtained by alkoxylation, preferably ethoxylation or propoxylation, of amines or higher-functionality amines, for example diamines or triamines. The starter compound used may, for example, be methylamine, ethylamine, isopropylamine, butylamine, benzylamine, aniline, toluidine, toluenediamine, naphthylamine, ethylenediamine, diethylenetriamine, 4,4'-methylenedianiline, propane-1,3-diamine, hexane-1,6-diamine, ethanolamine, diethanolamine, triethanolamine, ammonia or ethylenediamine or mixtures thereof. Here, the starter molecules are chosen and used in such amounts that the average nominal functionalities are obtained. The nominal functionality in the context of this invention is considered to be the functionality given solely by the functionality and the proportion of the starter molecules. Any reduction in the functionality, for instance by side reactions, is not taken into account.

Amine compounds (a2-II) preferably have a hydroxyl number of from 600 to 1100 mg KOH/g, particularly preferably 650 to 950 mg KOG/g. The amine compound having at least one tertiary nitrogen atom used is particularly preferably N,N,N',N'-tetrakis(2-hydroxypropyl)ethylenediamine, N,N,N',N'-tetrakis(2-hydroxyethyl)ethylenediamine or triisopropanolamine. In one particularly preferred embodiment, component (a2) comprises only one amine compound having at least one tertiary nitrogen atom, especially N,N,N',N'-tetrakis(2-hydroxypropyl)ethylenediamine, N,N,N',N'-tetrakis(2-hydroxyethyl)ethylenediamine or triisopropanolamine.

In one preferred embodiment, for the preparation of the polyurethane encapsulating compounds according to the invention, no organic tin compounds are used that are known as catalysts for the polyurethane reaction. More preferably, exclusively a bismuth catalyst is used as metal catalyst. In one very particularly preferred embodiment, the polyurethane catalyst used is exclusively the bismuth catalyst (a2).

Bismuth catalysts of this kind are disclosed, for example, in WO2016/114876 as catalysts for water-blown polyurethane foams, and are available commercially as Bicat® 8840 and Bicat® 8842 from Shepherd.

Besides components (a1) and (a2), further compounds may be present in polyol component (A), for example further polyols (a3). All polyols can be used here which are known in polyurethane chemistry and do not fall under the definition of components (a1). In one preferred embodiment, these do not have any tertiary nitrogen atoms. The polyol component (A) particularly preferably comprises at least one, at least difunctional, polyol (a3) which has a functionality of from 2 to 8 and a hydroxyl number of from 600 to 1350 mg KOH/g. These polyols (a3) can be obtained by alkoxylation, preferably ethoxylation or propoxylation, of difunctional or higher-functionality starter molecules, for instance ethylene glycol, diethylene glycol, propylene glycol, dipropylene glycol, glycerol, trimethylolpropane, pentaerythritol, sugar derivatives such as sucrose, hexitol derivatives such as sorbitol and also other dihydric or polyhydric alcohols, or mixtures thereof.

Here, the starter molecules are chosen and used in such amounts that the average nominal functionalities are obtained. The nominal functionality in the context of this invention is considered to be the functionality given solely by the functionality and the proportion of the starter molecules. Any reduction in the functionality, for instance by side reactions, is not taken into account.

In one further embodiment of the invention, compound a2-II can also be added to the system as a further component. Preferably, however, compound a2-II is not added to polyol component (A) as a further polyol.

The components (a1) to (a3) are preferably used in an amount such that the proportion of the fatty-acid-based polyol (a1) is 60 to 99% by weight, preferably 75 to 98% by weight and particularly preferably 90 to 96% by weight, the proportion of the bismuth catalyst (a2) is 0.001 to 2.0% by weight, preferably 0.001 to 1-5 by weight, more preferably 0.01 to 0.8% and particularly preferably 0.02 to 0.4% by weight, and the proportion of the polyol (a3) is 0 to 25% by weight, preferably 0.5 to 10% and particularly preferably 1.0 to 5% by weight, based in each case on the total weight of components (a1) to (a3). The polyol component (A) particularly preferably comprises, besides components (a1) to (a3), less than 20% by weight, particularly preferably less than 10% by weight and especially less than 5% by weight of further compounds, based in each case on the total weight of components (a1) to (a3). In a very particularly preferred embodiment, polyol component (A) comprises no further compounds besides compounds (a1) to (a3).

Isocyanate components (B) used may be any aromatic diisocyanates and higher-functionality isocyanates known in polyurethane chemistry. Preferably comprises the isocyanate prepolymers for preparing the polyurethane encapsulating compounds according to the invention. Such isocyanate prepolymers are obtained by reaction of diisocyanates and higher-functionality isocyanates (b1) with compounds having isocyanate-reactive groups (b2), preferably diols, where isocyanates are used in excess.

Isocyanate components b1) used are the customary aromatic di- and/or polyisocyanates or the mixtures thereof. Aromatic isocyanates here in the context of the present invention are isocyanates where an isocyanate group is bonded directly to a carbon atom in an aromatic system. Diisocyanates are especially suitable, for example tolylene diisocyanate (TDI). Diphenylmethane diisocyanates (hereinafter referred to as MDI) are preferred. Where MDI is used, all bicyclic isomers (2,2'; 2,4' and 4,4') can be used, optionally in a mixture with higher polycyclic homologs of diphenylmethane diisocyanate.

Isocyanate component b1) may additionally be present in modified form, for instance by incorporation of uretdione, carbamate, isocyanurate, carbodiimide, allophanate groups. Component b1) preferably comprises 2 to 10% by weight of a carbodiimide-modified isocyanate. A carbodiimide-modified 4,4'-MDI is particularly preferred here. Isocyanate component b1) very particularly preferably comprises 3 to 7% by weight of carbodiimide-modified 4,4'-MDI. The figures specified in % by weight of carbodiimide-modified isocyanate relate to a carbodiimide-modified isocyanate which comprises 10% by weight of carbodiimide. In the event of a different carbodiimide content, those skilled in the art will accordingly convert the specified values.

Diol components b2) used are organic polyhydroxy compounds having an OH functionality of from 1.5 to 2.5. The OH functionality is preferably in the range from 1.8 to 2.2; a diol compound having an OH functionality of 2 is particularly preferably used. In particular, alkoxylated diol compounds are preferred as diol component b2). Propylene glycols are particularly preferred as diol component b2).

Suitable propylene glycols include (mono)propylene glycol and dipropylene glycol and also oligo- and polypropylene glycols, where the latter may be prepared by propoxylation starting from a diol compound.

The modified isocyanate (B) preferably has an NCO content of from 12 to 30% by weight, particularly preferably of from 18 to 27% by weight and especially of from 20 to 25% by weight. Moreover, for the preparation of the polyurethane encapsulating compounds according to the invention, auxiliaries and/or additives may be used, such as cell regulators, separating agents, pigments, flame retardants, reinforcers such as glass fibers, surface-active compounds and/or stabilizers against oxidative, thermal, hydrolytic or microbial degradation or ageing. These are preferably added to the polyol component (A).

The conversion to the polyurethane encapsulating compound according to the invention is effected preferably without addition of blowing agent, so that the polyurethane according to the invention is a compact polyurethane. However, the polyols (a) used can in this case comprise small proportions of residual water. The residual water content is preferably below 1% by weight, more preferably below 0.3% by weight, particularly preferably below 0.05% by weight, based on the total weight of component (A) used. In one further embodiment of the invention, customary water scavengers are also added to the polyol component (A). If these are added, the proportion thereof is <20% by weight, preferably <10% by weight and very particularly preferably <5% by weight, based on the total weight of component (A). Particularly preferably, however, no water scavengers are used.

The feedstocks are also preferably chosen such that the resulting polyurethane encapsulating compounds can be sterilized by superheated steam and are non-cytotoxic. This is essentially brought about in that feedstocks are structured such that they either are incorporated into the polyurethane polymer lattice or can no longer migrate out of the polymer, and/or in that the solid polymer is so stable against hydrolysis that no low molecular weight degradation products that may be cytotoxic can be formed.

For the preparation of the polyurethanes according to the invention, generally the components (a) and (b) are reacted in amounts such that the ratio of equivalents of NCO groups to the sum total of reactive hydrogen atoms is 1:0.8 to 1:1.25, preferably 1:0.9 to 1:1.15. A ratio of 1:1 corresponds here to an NCO index of 100.

The starting components are typically mixed and reacted at a temperature of 0° C. to 100° C., preferably 15° C. to 70° C. The mixing can be effected with the conventional PUR processing machines. In one preferred embodiment, the mixing is effected by means of low-pressure machines or high-pressure machines. The encapsulating compounds are subsequently cast and subjected to curing, for example at temperatures of from 20 to 150° C., preferably 40 to 100° C.

Casting is to be understood as any measure that gives the initially free-flowing encapsulating compound that form which it has after the curing. Casting is in particular to be understood as the introduction into or application onto a body. Such a body may for example be a surface, a frame, a vessel with at least one opening or a mold with at least one depression. The encapsulating compound can in principle remain in contact with the body or be parted therefrom. The encapsulating compound is preferably not separated from the mold after curing has been carried out, but forms a unit with it.

The polyurethane encapsulating compounds according to the invention are used for preparing for encapsulating filter elements. To this end, a bundle of hollow fibers is embedded at their end in a polyurethane encapsulating compound according to the invention. Such a filter element can be used as water filter, for example for the treatment or purification of drinking water, or in the medical sector, for example as dialysis filter element.

The encapsulating compounds according to the invention feature good biocompatibility and low emission of substances, especially of toxic substances, rapid and uniform curing and good sterilizability.

The invention will be illustrated below with reference to examples.

Raw Materials Used
Poly 1: DAB castor oil from Alberdingk Boley
Poly 2: polyetherol based on trimethylolpropane and propylene oxide having an OH number of 935 mg KOH/g
Poly 3: polyetherol based on trimethylolpropane and propylene oxide having an OH number of 160 mg KOH/g
Poly 4: oleochemical polyester (Sovermol 819) having an OH number of 240 mg KOH/g
Poly 5: polyetherol based on glycerol and propylene oxide having an OH number of 805 mg KOH/g
Poly 6: triisopropanolamine
Poly 7: N,N,N',N'-tetrakis(2-hydroxypropyl)ethylenediamine
CE1: oxydipropanol
CE2: 2-methyl-1,3-propanediol
CE3: monoethylene glycol
ISO1: isocyanate prepolymer based on MDI, dipropylene glycol and polypropylene glycol and having an NCO content of 23% by weight
ISO2: isocyanate prepolymer based on MDI, dipropylene glycol, polypropylene glycol and castor oil and having an NCO content of 20.6% by weight
Cat 1: Tinstab OTS 16 tin catalyst from Akcros
Cat 2: Coscat 83 bismuth catalyst
Cat 3: Bicat 8118M bismuth catalyst from Shepherd
Cat 4: Bi 2010L bismuth catalyst from Umicore
Cat 5: Bicat 8840 bismuth catalyst from Shepherd, prepared from bismuth neodecanoate and N,N,N',N'-tetrakis(2-hydroxypropyl)ethylenediamine
Cat 6: Bicat 8842 bismuth catalyst from Shepherd, prepared from bismuth neodecanoate and N,N,N',N'-tetrakis(2-hydroxyethyl)ethylenediamine For the determination of the storage stability of the polyol mixture, polyols and catalysts were mixed as indicated in tables 1 to 3 to give a polyol component; all figures in the tables correspond to parts by weight unless otherwise indicated. The polyol components obtained were stored as indicated at room temperature and with the exclusion of air in a sealed container. Prior to sampling, the mixture was homogenized and then degassed. The first measurement for determining the starting reactivity was conducted 24 hours after the polyol mixture had been made up, so that the system could settle. After that, the gel time was determined at various intervals.

The gel time was determined here as follows. The required amount of isocyanate at an isocyanate index of 105 was added to a corresponding amount of polyol mixture. The amounts of the isocyanate component and the polyol component were selected here such that 100 g of reaction mixture were obtained. The reaction mixture was mixed in a Speedmixer™ PP130 cup at 25° C. for 30 s at 1800 rpm by means of a Speedmixer™ from Haunschild and at the same time measurement was started on a SHYODU Gel Timer. After the mixing time of 30 seconds the PP130 cup was placed beneath the Gel Timer and the gel time was determined. The gel time is determined here as the time in which the viscosity of the reaction mixture at constant temperature increases to such an extent that the stirring force required exceeds the stirring force provided by the Shyodu Gel Timer.

The following examples are intended to illustrate the effect of the composition according to the invention.

TABLE 1

|  | C1 | C2 | C3 | C4 |
|---|---|---|---|---|
| Poly 1 | 100 | 95.0 | 90.0 | 85.0 |
| Poly 2 |  |  |  |  |
| Poly 7 |  | 5.0 | 10.0 | 15.0 |
| Cat 1 |  |  |  |  |
| Iso 1 | X | X | X | X |
| Iso 2 |  |  |  |  |
| Hardness [Shore D] | 18 | 56 | 70 | 76 |
| Gel time [hh:mm:ss] |  |  |  |  |
| 1 d | 01:14:06 | 00:38:11 | 00:19:10 | 00:08:16 |
| 14 d |  |  |  |  |

As is apparent from comparative examples C1 to C4, the use of N,N,N'',N''-tetrakis(2-hydroxypropyl)ethylenediamine leads to a shortening of the open time and thus to an increase in the reactivity. However, rapid cycle times can only be achieved with high concentrations of N,N,N'',N''-tetrakis(2-hydroxypropyl)ethylenediamine. This has the disadvantage though that the systems show a distinct gain in hardness and hence the cuttability of the systems suffers.

|  | C5 | C6 | C7 | C8 | C9 | C10 | C11 |
|---|---|---|---|---|---|---|---|
| Poly 1 | 94.92 | 94.9 |  | 94.9 |  | 94.9 |  |
| Poly 2 | 5.00 | 5.0 | 5.04 | 5.0 | 5.04 | 5.0 | 5.04 |
| Poly 3 |  |  | 94.91 |  | 94.91 |  | 94.95 |
| Cat 1 | 0.08 |  |  |  |  |  | 0.01 |
| Cat 2 |  | 0.1 | 0.05 |  |  |  |  |
| Cat 3 |  |  |  | 0.1 | 0.05 |  |  |
| Cat 4 |  |  |  |  |  | 0.1 |  |
| Iso 1 |  | X | X |  | X |  | X |
| Iso 2 | X |  |  | X |  | X |  |
| Mixing ratio 100:X | 76.9 | 69.1 | 69.8 | 76.9 | 69.8 | 76.9 | 69.9 |

-continued

| | C5 | C6 | C7 | C8 | C9 | C10 | C11 |
|---|---|---|---|---|---|---|---|
| Gel time [mm:ss] | | | | | | | |
| 1 d | 03:20 | 03:29 | 00:48 | 07:10 | 01:05 | 07:20 | 05:20 |
| 7 d | n.m. | n.m. | 00:51 | n.m. | 01:05 | 11:00 | n.m. |
| 14 d | n.m. | 04:48 | n.m. | n.m. | n.m. | n.m. | n.m. |
| 56 d | 3:05 | 08:45 | 00:58 | 11:30 | 01:20 | >16:00 | 05:30 |

As can be seen from comparative examples C5 & C11, the use of tin catalysts in compact polyurethane systems leads to storage-stable mixtures having stable reactivity irrespective of whether oleochemical polyols are used in the system. Examples C7 and C9 clearly show that bismuth catalysts can be used as a suitable replacement for tin catalysts in compact polyurethane systems not comprising any oleochemical polyols. The reactivity of the systems also remains virtually constant here. Comparative examples C6, C8 & C10 reveal that the reactivity of systems comprising fatty acid polyols can decrease greatly over time and that bismuth carboxylates cannot be used as a suitable replacement for tin catalysts in such systems.

TABLE 3

| | E1 | E2 | E3 | E4 |
|---|---|---|---|---|
| Poly 1 | 94.90 | 94.80 | 89.27 | 15.00 |
| Poly 2 | 5.00 | 5.00 | 2.78 | |
| Poly 4 | | | | 78.35 |
| Poly 5 | | | | 4.50 |
| CE 1 | | | 7.87 | |
| CE 2 | | | | 2.00 |
| Cat 5 | | 0.20 | | |
| Cat 6 | 0.10 | | 0.09 | 0.15 |
| Iso 1 | X | | X | X |
| Iso 2 | | X | | |
| Mixing ratio 100:X | 69.2 | 76.8 | 81.8 | 96.5 |
| Gel time [mm:ss] | | | | |
| 1 d | 04:53 | 03:20 | 03:10 | 04:27 |
| 28 d | n.m. | 03:23 | 03:21 | 04:10 |
| 56 d | 04:41 | n.m. | 03:12 | 04:37 |

Examples E1 to E4 show that, through the use of a catalyst based on bismuth carboxylates and alkanolamines, storage-stable mixtures with oleochemical polyols can be obtained.

Besides N,N,N',N'-tetrakis(2-hydroxypropyl)ethylenediamine and N,N,N',N'-tetrakis(2-hydroxyethyl)ethylenediamine, other alkanolamines can also be used for the preparation of stable bismuth catalysts. This shall be explained by the following example.

EXAMPLE E5

A 250 ml four-neck flask with thermometer, stirrer, condenser and nitrogen feed was initially charged with 75.00 g of Cat 3 and heated to 60° C. 44.23 g of molten Poly 6 was then added slowly to the catalyst while stirring. At the end of addition, the mixture was stirred further for an additional 15 minutes and 30 g of CE 3 were added. The mixture was then decanted and used for further experiments. These reaction products likewise displayed good storage stability and constant reactivity, as the appended example 6 shows:

TABLE 3

| | E6 |
|---|---|
| Poly 1 | 94.90 |
| Poly 2 | 5.00 |
| Cat from example E5 | 0.10 |
| Iso 1 | X |
| Mixing ratio 100:X | 69.2 |
| Gel time [mm:ss] | |
| 1 d | 06:21 |
| 14 d | 06:18 |
| 90 d | 06:12 |

The invention claimed is:

1. A polyurethane encapsulating compound for embedding hollow fibers of filter elements, obtained by mixing a polyol component (A) and an isocyanate component (B), comprising at least one aromatic isocyanate, to give a reaction mixture and reacting the mixture to completion to give the polyurethane encapsulating compound,
wherein the polyol component (A) comprises
(a1) at least one fatty-acid-based polyol having a hydroxyl number of greater than 50 to less than 500 mg KOH/g and a functionality of from 2 to 6
(a2) at least one bismuth catalyst, obtained by mixing a bismuth carboxylate (a2-1) with an amine compound (a2-11) having at least one tertiary nitrogen atom and at least one isocyanate-reactive hydrogen atom, wherein the molar ratio of bismuth to the amine compound (a2-11) is 1:0.5 to 1:50; and
(a3) at least one polyol which has a functionality of from 2 to 8 and a hydroxyl number of from 600 to 1350 mg KOH/g and does not have a tertiary nitrogen atom,
wherein the fatty-acid-based polyol (a1) is present in a proportion of 60 to 98% by weight, the bismuth catalyst (a2) is present in a proportion of 0.001 to 1.0% by weight and the polyol (a3) is present in a proportion of 0.5 to 10% by weight, based in each case on the total weight of components (a1) to (a3).

2. The polyurethane encapsulating compound according to claim 1, wherein the amine compound (a2-11) has at least three isocyanate-reactive hydrogen atoms.

3. The polyurethane encapsulating compound according to claim 1, wherein the amine compound (a2-11) is an alkoxylated amine having a hydroxyl number of from 500 to 1200 mg KOH/g and having 3 to 6 hydrogen atoms that are reactive toward isocyanate groups.

4. The polyurethane encapsulating compound according to claim 3, wherein the amine compound (a2-11) is a diamine-started propylene oxide having a nominal functionality of from 3 to 6 and a hydroxyl number of from 500 to 900 mg KOH/g.

5. The polyurethane encapsulating compound according to claim 1, wherein the fatty-acid-based polyol (a1) comprises castor oil or the alkoxylation product of castor oil.

6. The polyurethane encapsulating compound according to claim 1, wherein the isocyanate component (B) comprises prepolymers of isomers and/or homologs of diphenylmethane diisocyanate.

7. A method for producing filter elements in which a bundle of hollow fibers is embedded and cured in a polyurethane encapsulating compound according to claim 1.

8. The method according to claim 7, wherein the filter element is a filter element for use in medicine.

9. The method according to claim 8, wherein the filter element is a dialysis filter element.

10. The method according to claim 7, wherein the filter element is a water filter element.

11. The method according to claim 7, wherein the bundle of hollow fibers is partially embedded in the polyurethane encapsulating compound.

12. The method according to claim 1, wherein the polyurethane encapsulating compound has a density from 0.8 g/l to 1.3 g/l.

13. The polyurethane encapsulating compound according to claim 5, wherein the bismuth carboxylate (a2-1) is bismuth(III) neodecanoate, the amine compound (a2-11) is N,N,N',N'-tetrakis(2-hydroxypropyl)ethylenediamine or N,N,N',N'-tetrakis(2-hydroxypropyl)ethylenediamine, and the molar ratio of bismuth to the amine compound (a2-11) is 1:2 to 1:5; and the polyol (a3) is obtained by propoxylation of trimethylolpropane or glycerol, wherein the fatty-acid-based polyol (a1) is present in a proportion of 75 to 98% by weight, the bismuth catalyst (a2) is present in a proportion of 0.02 to 0.4% by weight and a polyol (a3) is present in a proportion of 1.0 to 5% by weight.

* * * * *